US006593317B1

(12) United States Patent
de Ziegler et al.

(10) Patent No.: US 6,593,317 B1
(45) Date of Patent: Jul. 15, 2003

(54) PROGESTIN THERAPY FOR MAINTAINING AMENORRHEA

(75) Inventors: Dominique de Ziegler, Paris (FR); William J. Bologna, Paris (FR); Howard L. Levine, Oceanside, NY (US)

(73) Assignee: Columbia Laboratories, Inc., Livingston, NJ (US)

( * ) Notice: Subject to any disclaimer, the term of this patent is extended or adjusted under 35 U.S.C. 154(b) by 103 days.

(21) Appl. No.: 09/833,259

(22) Filed: Oct. 17, 2000

Related U.S. Application Data

(62) Division of application No. 09/170,326, filed on Oct. 13, 1998, now Pat. No. 6,306,914
(60) Provisional application No. 60/063,485, filed on Oct. 21, 1997.

(51) Int. Cl.[7] ................... A61K 31/57; A61K 47/32; A61P 5/34

(52) U.S. Cl. ............... 514/177; 514/899; 514/772.6; 424/487

(58) Field of Search ............... 514/899, 944, 514/177, 170, 772.6; 424/487

(56) References Cited

U.S. PATENT DOCUMENTS

| | | |
|---|---|---|
| 4,615,697 A | 10/1986 | Robinson |
| D345,211 S | 3/1994 | Bologna |
| 5,543,150 A | 8/1996 | Bologna et al. |
| D375,352 S | 11/1996 | Bologna |

FOREIGN PATENT DOCUMENTS

| | | |
|---|---|---|
| WO | WO 95/07699 | 3/1995 |

OTHER PUBLICATIONS

Adlercreutz, H. et al., "Biliary Excretion and Intestinal Metabolism of Progesterone and Estrogens in Man," J. Steroid Biochem, vol. 13, pp. 231–244, Pergamon Press Ltd 1980.

Al–Azzawi, F. et al., "Vaginal progesterone gel–based continuous combined HRT as an amenorrheic regimen," European Congress on Menopause, Vienna, Austria, Oct. 8–12, 1997.

Al–Azzawi, F. et al., "Investigation of the bleeding patterns of postmenopausal women treated with Estrapak–50," Maturitas 18 (1994) 115–125.

Archer, D.F. et al., "Bleeding Patterns in Postmenopausal Women Taking Continuous Combined or Sequential Regimens of Conjugated Estrogens With Medroxyprogesterone Acetate," Obstetrics & Gynecology, vol. 83, No. 5, Part 1, May 1994, 686–692.

Barrett–Connor, E., "The menopause, hormone replacement, and cardiovascular disease: the epidemiologic evidence," Maturitas 23 (1996) 227–234.

Bourgain, C. et al., "Effects of natural progesterone on the morphology of the endometrium in patients with primary ovarian failure," Human Reproductin, vol. 5, No. 5 (1990) 537–543.

Bulleti, C. et al., "Targeted drug delivery in gynaecology: the first uterine pass effects," Human Reproduction,, vol. 12, No. 5 (1997) 1073–1079.

(List continued on next page.)

*Primary Examiner*—Edward J. Webman
(74) *Attorney, Agent, or Firm*—Winston & Strawn

(57) ABSTRACT

The present invention teaches that daily, cyclical vaginal delivery of progestin may be used to provide regular, predictable withdrawal bleeding during hormone replacement therapy. The present invention also teaches that constant administration of progestin in a water-insoluble, water-swellable cross-linked polycarboxylic acid polymer may be used to maintain amenorrhea. Either regimen is accompanied by a significant decrease in adverse side effects.

11 Claims, 3 Drawing Sheets

OTHER PUBLICATIONS

Burch, D.J. et al., "A dose–ranging study of the use of cyclical dydrogesterone with continuous 17β oestradiol," Brit. J. Obstet. and Gynecol., vol. 102 (Mar. 1995) 243–248.

Byrjalsen, I. et al., "Secretory endometrial protein PP14 in serum from post–menopausal women receiving continuous combined oestradiol–cyproterone acetate: Correlation with serum hormone concentrations and bleeding patterns," Maturitas 15 (1992) 39–46.

Casanas–Roux, F. et al., "Morphometric, Immunohistological and Three–Dimensional Evaluation of the Endometrium of Menopausal Women Treated by Oestrogen and Crinone, a New Slow–Release Vaginal Progesterone", Human Reproduction, vol. 11, No. 2, 1996, pp. 357–363, XP002094220.

Caudron, J. et al., "Comparison of two equine oestrogen–dydrogesterone regimens in the climacteric," Maturitas 10 (1988) 133–141.

Clisham, P.R. et al., "Comparison of Continuous Versus Sequential Estrogen and Progestin Therapy in Postmenopausal Women," Acta Obstetrics & Gynecology, vol. 77, No. 2 (Feb. 1991) 241–246.

Croxatto, H.B. et al., "Plasma progesterone levels following subdermal implantation of progesterone pellets in lactating women," Acta Endocrinologica 1982, 100:630–633.

deZiegler, D. et al., "Effects of Luteal Estradiol on the Secretory Transformation of Human Endometrium and Plasma Gonadotropins," J. Clin. Endocrin. and Metab., vol. 74, No. 2 (1992) 322–331.

Dören, M. et al., "Superior compliance and efficacy of continuous combined oral estrogen–progestogen replacement therapy in postmenopausal women," Am. J. Obstet. Gynecol., vol. 173, No. 5 (Nov. 1995) 1446–1451.

Fahraeus, L., "L–norgestrel and progesterone have different influences on plasma lipoproteins," European Journal of Clinical Investigation, vol. 13, No. 6, Dec. 1983, XP002055334.

Fanchin, R. et al., "Transvaginal Administration of Progesterone," Obstetrics & Gynecology, vol. 90, No. 3, (Sep. 1997) 396–401.

Fraser, D.J. et al., "The optimal dose of oral norethindrone acetate for addition to transdermal estradiol: a multicenter study," Fertility and Sterility, vol. 53, No. 3 (Mar. 1990) 460–468.

Grey, A.B. et al., "Continuous combined oestrogen/progestin therapy in well tolerated and increases bone density at the hip and spine in post–menopausal osteoporosis," Clinical Endocrinology (1994), 40, 671–677.

Grodstein, F. et al., "Postmenopausal Estrogen and Progestin Use and the Risk of Cardiovascular Disease," New England Journal and Medicine, vol. 335, No. 7 (Aug. 15, 1996) 453–461.

Babiba, M.A. et al., "Endometrial responses with estrogen replacement: Withdrawal bleeding and othe factors," Am. J. Obstet. Gynecol, vol. 161, No. 6, Part 2 (Dec. 1989) 1854–1858.

Hillard, T.C. et al., "Continuous combined conjugated equine estrogen–progestogen therapy: Effects of medroxyprogesterone acetate and norethindrone acetate on bleeding patterns and endometrial histologic diagnosis," Am. J. Obstet and Gynecol, vol. 167, No. 1 (Jul. 1992) 1–7.

Høvik, H.P. et al., "Comparison of continuous and sequential oestrogen–progestogen treatment in women with climacteric symptoms," Maturitas 11 (1989) 75–82.

Hulley, S. et al., "Randomized Trial of Estrogen Plus Progestin for Secondary Prevention of Coronary Heart Disease in Postmenopausal Women," J. Am. Med. Assn. 280 (1998) 605–613.

Jensen, J. et al., "Long–term and withdrawal effects of two different oestrogen–progestogen combinations on lipid and lipoprotein profiles in post–menopausal women," Maturitas 11 (1989) 117–128.

Lindsay, R. et al., "Therapeutic Controversy: Estrogen Replacement in Menopause," J. Clin. Endocrin and Metab, vol. 81, No. 11 (1996) 3829–3838.

Lobo, R.A., "The role of progestins in hormone replacement therapy," Am. J. Obstet Gynecol, vol. 166, No. 6, Part 2 (Jun. 1992) 1997–2004.

MacLennan, A.H. et al., "Continuous low–dose oestrogen and progestrogen hormone replacement therapy: a randomised trial," The Medical Journal of Australia, vol. 159 (Jul. 1993) 102–106.

Magos, A.L. et al., "Amenorrhea and Endometrial Atrophy With Continuous Oral Estrogen and Progestogen Therapy in Postmenopausal Woment," Obstetrics & Gynecology, vol. 63, No. 4 (Apr. 1985) 496–499.

Marslew, U. et al., "Bleeding patterns during continuous combined estrogen–progesterone therapy," Am. J. Obstet Gynecol, vol. 164 No. 5, Part 1 (May 1991) 1163–1168.

Mauvais–Jarvis, P. et al., "In Vivo Studies on Progesterone Metabolism by Human Skin," J. Clin Endocr vol. 29 (Dec. 1969) 1580–1585.

Maxson, W.S. et al., "Bioavailability of oral micronized progesterone," Fertility and Sterility vol. 44, No. 5 (Nov. 1985) 622–626.

Maxson, W.S., "The Use of Progesterone in the Treatment of PMS," Clin Obstet and Gynecol, vol. 30, No. 2 (Jun. 1987) 465–477.

Miles, R.A. et al., "Pharmacokinetics and endometrial tissue levels of progesterone after administration by intramuscular and vaginal routes: a comparative study," Fertility and Sterility, vol. 62, No. 3 (Sep. 1994) 485–490.

Moyer, D.L. et al., "Prevention of endometrial hyperplasia by progesterone during long–term estradiol replacement: influence of bleeding pattern and secretory changes," Fertility and Sterility, vol. 59, No. 5 (May 1993) 992–997.

Navot, D. et al., "Artificially Induced Endometrial Cycles and Establishment of Prognancies in the Absence of Ovaries," The New England Journal of Medicine, vol. 314, No. 13 (Mar. 1986) 806–811.

Navot, D. et al., "An Insight into Early Reproductive Processes through in Vivo Model of Ovum Donation," J. Clin. Endocrin and Metab, vol. 72, No. 2 (1991) 408–414.

Niles, L. et al., "The pathophysiology of peri–and postmenopausal bone loss," Br J Obstet Gynaecol May 1989 96(5): 580–587.

Nillius, S.J. et al., "Plasma levels of progesterone after vaginal, rectal, or intramuscular administration of progesterone," Am. J. Obstet. Gynec., vol. 110, No. 4 (Jun. 1971) 470–477.

Panay, N. et al., "Progestogen intolerance and compliance with hormone replacement therapy in menopausal women," Human Reproduction Update, vol. 3, No. 2 (1997) 159–171.

Ravnikar, V.A., "Complaince with hormone therapy," Am. J. Obstet. Gynecol., vol. 156, No. 5 (May 1987) 1332–1334.

Rosano, G.M.C. et al., "Medroxyprogesterone but not natural progesterone reverses the beneficial effect of estradiol 17beta exercise–induced myocardial ischemia," Supp. to Circulation, vol. 94, No. 8 (Oct. 1996) Abstracts from the 69th Scientific Sessions, New Orleans Convention Center, New Orleans, LA, Nov. 10–13, 1996, Abstract 0104.

Rosano, G.M.C. et al., "Medroxyprogesterone acetate (MPA) but not natural progesterone (P) reverses the effect of estradiol 17β (E2) upon exercise–induced myocardial ischemia. A double–blind cross–over study," Menopause, Abstracts, 8th International Congress on the Menopause, Nov. 3–7, 1996, Sydney, Australis, Abstract No. F126.

Rosenwaks, Z., "Donor eggs: their application in modern reproductive technologies," Fertility and Sterility, vol. 47, No. 6 (Jun. 1987) 895–909.

Ross, D. et al., "Endometrial effects of three doses of trimegestone, a new orally active progestogen, on the postmenopausal endometrium," Maturitas 28 (1997) 83–88.

Rozenbaum, H. et al., "Continuous HRT with oral 17βE2 and promegestone: results of a one–year trial with 3 dose regimen," The North American Menopause Society, 6th Annual Meeting, San Francisco, CA, Sep. 21–23, 1995.

Saure, A. et al., "A randomized double–blind, multicentre study comparing the clinical effects of two sequential estradiol–progestin combinations containing either desogestrel or norethisterone acetate in climacteric women with estrogen deficiency symptoms," Maturitas 24 (1996) 111–118.

Siddle, N.C. et al., "Endometrial, physical and psychological effects of postmenopausal oestrogen therapy with added dydrogesterone," Br. J. Obstet and Gynaecol, vol 97, (Dec. 1990) 1101–1107.

Simon, J.A. et al., "The absorption of oral micronized progesterone: the effect of food, dose proportinality, and comparison with intramuscular progesterone," Fertility and Sterility, vol. 60, No. 1 (Jul. 1993) 26–33.

Sitruk–Ware, L.R. et al., "Inadequate Corpus Luteal Function in Women with Benign Breast Diseases," J. Clin Endocrinol & Metab, vol. 44, No. 4 (1977) 771–774.

Thomas, J.L. et al., "Postmenopausal hormone replacement therapy with estrogens and nomegestrol acetate. A multicentric study," 7th International Congress on the Menopause, Jun. 20–24, 1993, Stockholm, Sweden.

Toner, J.P. et al., "Crinone 8% Used Once a Day for Replacement in Donor Egg Recipients: A Status Report," IFFS '98/American Society for Reproductive Medicine, Abstract.

van der Mooren, M.J. et al., "Changes in the withdrawal bleeding pattern and endometrial histology during 17β–estradiol–dydrogesterone therapy in postmenopausal women: a 2 year prospective study," Maturitas 20 (1995) 175–180.

Villanueva, B. et al., "Pilot Study of Continuous Combined Postmenopausal HRT Using Alternate Day or Twice Weekly Vaginal Progesterone" Maturitas, vol. 27, No. Suppl, F015, 1997, p. 47 XP002094218.

Warren, M.P. eta l., "Evaluation of Crinone®, A Transvaginally Administered Progesterone Containing Bioadhesive Gel in Women with Secondary Amenorrhea," Maturitas, Supplement: 8th International Congress on the Menopause, Nov. 3–7, 1996, Syndey, Australia, Abstract F168.

Weinstein, M. et al., "Hormone Replacement Therapy Your Questions Answered," (Churchill Livingstone Publishers, Edinburgh 1992), Chapters 5 & 9.

Casper, R.F., "Regulation of Estrogen/Progestogen Receptors in the Endometrium," Int. J. Fertil., vol. 4(1), pp. 16–21 (1996).

McKinlay, S.M., et al., "The normal menopause transition," Maturitas, vol. 14, pp. 103–115 (1992).

Nakamura, S., et al., "Relationship Between Sonographic Endometrial Thickness and Progestin–Induced Withdrawal Bleeding," Obstetrics and Gynecology, vol. 87(5), part 1, pp. 722–725 (1996).

Rarick, L.D., et al., "Cervical mucus and serum estradiol as predictors of response to progestin challenge," Fertility and Sterility, vol. 54(2), pp. 353–355 (1990).

Speroff, L., et al., "Dysfunctional Uterine Bleeding," Clinical Gynecologic Endocrinology and Infertility, Chapter 16, pp. 531–546, 5th Edition, 1994 (Williams and Wilkins).

Valenzuela, P., et al., "Progestin challenge test in postmenopausal patients," Int. J. Gynecol. Obstet., vol. 43, pp. 313–316 (1993).

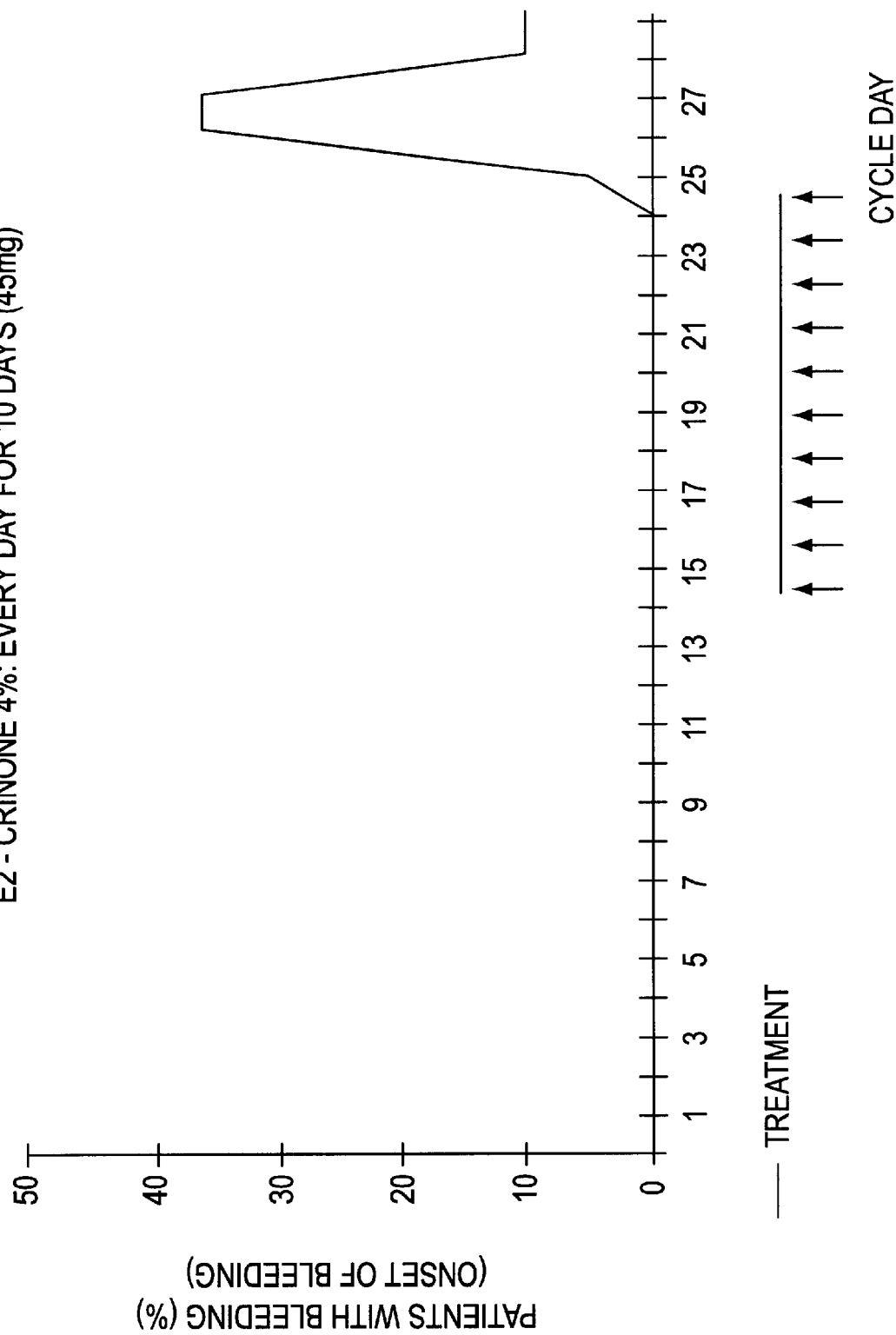

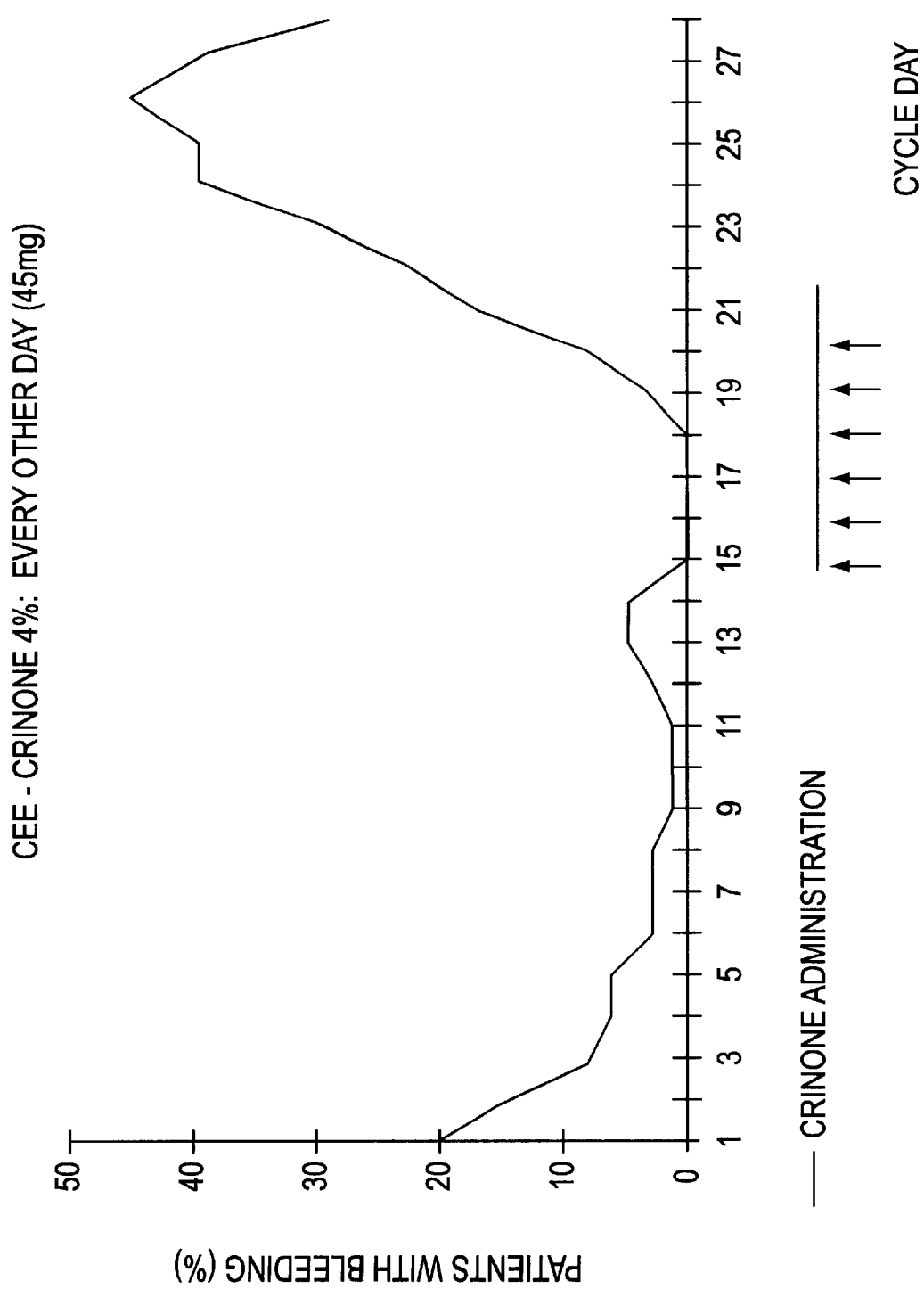

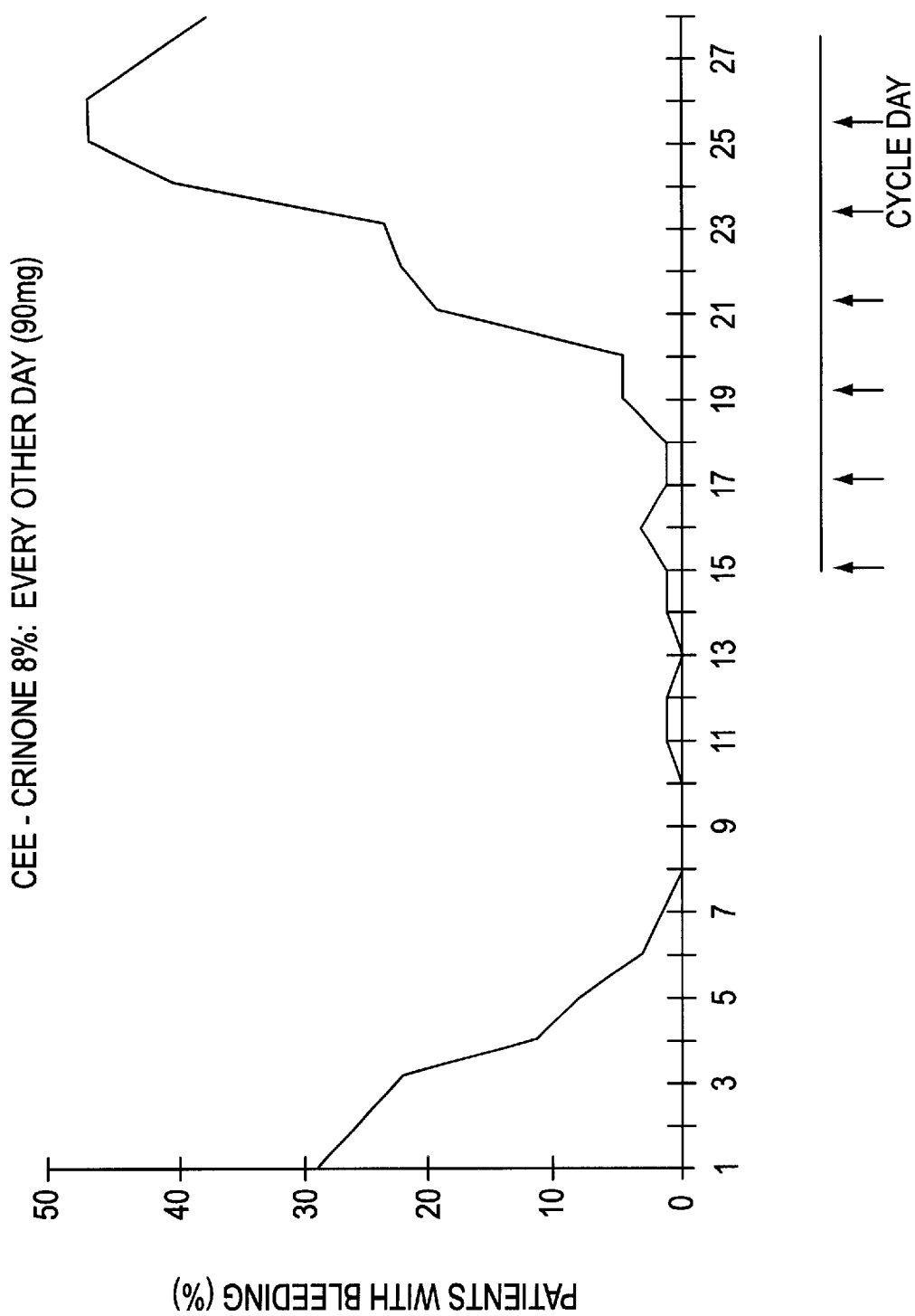

PROGESTIN THERAPY FOR MAINTAINING AMENORRHEA

This application is a divisional of U.S. patent application Ser. No. 09/170,326, filed Oct. 13, 1998, now U.S. Pat. No. 6,306,914 which, in turn, claims the benefit of U.S. Patent Provisional Application No. 60/063,485, filed Oct. 21, 1997, which is incorporated herein by reference.

FIELD OF THE INVENTION

This invention relates to a method of administering progestin therapy in a manner that promotes controlled bleeding, rather than the irregular and unpredictable bleeding that normally accompanies progestin administration.

BACKGROUND OF THE INVENTION

Progesterone is a naturally occurring steroid which is the main steroid secreted by women during their reproductive years. This steroid has been studied extensively and has been found to be a major precursor in the biosynthesis of most other steroids, particularly glucocorticoids, androgens and estrogens. Progesterone also stimulates the growth of the uterus and a number of specific changes in the endometrium and myometrium. It is essential for the development of decidual tissue and the differentiation of luminal and glandular epithelial tissue. Progesterone also plays several roles in gestation, including breast enlargement, inhibition of uterine contractility, maintenance of gestation, immunological protection of the embryo, and inhibition of prostaglandin synthesis.

Progestins include the natural progestin, progesterone, as well as the synthetic progestins, such as medroxyprogesterone acetate (MPA). Progestins have been used pharmaceutically in the treatment of a number of clinical disorders such as luteal phase deficiency, dysfunctional uterine bleeding, endometriosis, endometrial carcinoma, benign breast disease, pre-eclampsia, and assisting in vitro fertilization, preventing early abortion and reducing the occurrence of endometrial hyperplasia in estrogen replacement therapy (ERT).

The most common progestational agents used are the synthetic progestins, which are accompanied by undesirable side effects such as depression and water retention. Additionally, many of the synthetic progestins derived from 19-nor-testosterone reverse the positive effects of estrogen on lipoprotein (HDL) levels. In contrast, natural progesterone does not cause water retention, is rarely associated with depression and has no adverse effects upon lipid levels.

There have been many difficulties in administering natural progesterone at the appropriate serum and tissue levels to patients. When given orally, progesterone is rapidly metabolized. See e.g., Adlecruz, H. and Martin, F. J. *Steroid Biochem.*, 13: 231–244 (1980) and Maxson, W. S., and Hargrove, J. T., *Fertil. Steril.*, 44: 622–626 (1985).

Rectal administration of progestins has also been attempted with 25 mg and 100 mg doses of natural progesterone, which achieved peak plasma levels at 4 to 8 hours after administration followed by a gradual decline, but the maintenance of a stable plasma level has been difficult with this route. Maxson, W. S. *Clinical Obstet. Gynecol.*, 30: 465–477 (1987); Nillius, S. J. and Johansson, E. D. B. *Am. J. Obstet. Gynecol.*, 110: 470–479 (1971). Sublingual administration resulted in rapid appearance of progesterone in the serum reaching peak values of up to 10 times basal levels, but returning to basal levels within twenty-four hours. Villanueva, B., et al., *Fertil. Steril.*, 35: 433–437 (1981). Nasal administration, using 20 mg and 30 mg doses, achieved mean maximum concentrations of 2.1 and 4.1 ng/ml, respectively, at approximately 30 and 240 minutes, respectively.

Intramuscular administration of progesterone has been attempted with 100 mg doses which achieved 40 to 50 ng/ml serum concentrations in two to eight hours. Nillius, S. J. and Johansson, E. D. B., *Am. J. Obstet. Gynecol.*, 110: 470–479 (1971). Such administration has shown that such injections need to be given every day or on alternate days to produce results. Whitehead, M., and Godfree, V. in *Hormone Replacement Therapy, Churchill Livingston Edinburgh* 1992, pp 91. Subdermal administration has also been assayed, with six 100 mg progesterone pellets being implanted in postpartum women. Croxatto, H. B., et al., *Acta Endocrinol*, 100: 630 (1982). Progesterone levels reached a peak of 4.4 ng/ml within the first week after insertion and reached a mean peak level of 1.9 ng/ml six months after implantation. Progestin implants are not practical in cyclical therapy and moreover, physiological levels of progestin are not achieved. ("Cyclical" therapy means that the progestin is administered off and on, typically for a portion of each 28-day cycle or each calendar month. For example, cyclical administration could be daily, or every other day, only on days 15 through 20 of each 28-day cycle, or only for the first five days each month. "Constant" or "continuous" therapy means that the drug is administered regularly, whether it is daily, every other day, weekly, or otherwise, without regard, for example, to the 28-day cycle or the calendar month.)

It has been demonstrated that topically applied radioactive progesterone can be absorbed through the skin. Mauvais-Jarvis, Progesterone., et al., *J. Clin. Endocrinol. Metab.*, 29: 1580–1587 (1969). Labeled metabolites were recovered in the urine at 48 hours after topical administration. However, the absorption was only 10% of the applied dose. The high fat solubility of progesterone is responsible for the prolonged retention of this steroid and the extensive local metabolism reduces the systemic effect of the steroid. It has been shown that treatment with topical application of progesterone to the breast produces no significant endometrial effects. Sitruk-Ware, R., et al., *J. Clin. Endocrin. Metab.*, 44: 771–774 (1977).

Progestins have also been administered vaginally to postmenopausal women receiving ERT. 50 mg/ml of progesterone in a suspension containing carboxymethyl cellulose and methyl cellulose which was inserted into the vagina was characterized by a rapid absorption of the progesterone across the vaginal mucosa. There was an immediate appearance of the hormone in the peripheral circulation resulting in a 10-fold increase over the baseline serum levels (0.34 ng/ml) after 15 minutes. The peak levels were obtained 1 or 2 hours after administration and represented a thirty- to forty-fold increase over baseline levels (12.25 ng/ml). The serum levels remained at this level over the next seven hours, declining over the next ten hours to 3.68 ng/ml. Villanueva, B., et al., *Fertil. Steril.*, 35: 433–437 (1981). These results suggested that the absorption of progestins was enhanced in women also undergoing ERT.

As described in U.S. Pat. No. 5,543,150 ("the '150 Patent"), which is incorporated herein by reference, it now appears that the bioadhesive formulation used with the instant invention can provide local vaginal administration of progestins to yield significant local drug levels while maintaining serum levels low enough to avoid most of the undesired side effects. See also, Warren, M. P., et al., *Evaluation of Crinone®, a Transvaginally Administered Progesterone Containing Bioadhesive Gel, in Women with*

Secondary Amenorrhea, Abstract, Presented at the 8th International Congress on the Menopause, Sydney, Australia, 1996. And as described in U.S. patent application Ser. No. 08/743,153, which is incorporated herein by reference, it also appears that progesterone can be administered for the purpose of treating or reducing ischemia or incidence of cardiovascular events.

Treatments of menopausal and post-menopausal women involving administration of progestins in cyclical association with estrogen induces the physiological sequence of endometrial changes normally encountered in the menstrual cycle. Such treatments usually administer progestins, usually daily, over a period of about 10 to 14 days each month. However, the withdrawal bleeding that results from such administration is typically irregular and unpredictable, and often begins as early as about the fourth day following the first progestin dose. See, Archer, D. F., et al., *Bleeding Patterns in Post-menopausal Women Taking Continuous Combined or Sequential Regimens of Conjugated Estrogens with Medroxyprogesterone Acetate, Obstet. Gynecol.*, 83: 686–92 (1994).

SUMMARY OF THE INVENTION

The present invention comprises a method of cyclical vaginal administration of progestins daily, while avoiding significant adverse side effects, in order to avoid the often-erratic monthly withdrawal bleeding normally associated with cyclical progestin treatment, and instead to provide regular withdrawal bleeding upon completion of the progestin-administration period. Thus the invention provides the benefits of cyclical progestin therapy without the inconvenience and complications of irregular withdrawal bleeding, and without common side effects.

The present invention also comprises a method of constant vaginal administration to maintain complete amenorrhea while avoiding significant adverse side effects. Thus, the invention provides complete amenorrhea without the periodic breakthrough bleeding or spotting often observed with other methods for three to six months, and without significant adverse side effects often resulting from other methods.

BRIEF DESCRIPTION OF THE DRAWINGS

FIG. 1 illustrates the bleeding pattern produced by a 45 mg. dose of progestin (CRINONE® 4% progesterone gel) cyclically administered every day vaginally.

FIG. 2 illustrates the bleeding pattern produced by a 45 mg. dose of progestin (CRINONE® 4% progesterone gel) cyclically administered every other day vaginally, as reported in Warren, M. P., et al., *Evaluation of Crinone®, a Transvaginally Administered Progesterone Containing Bioadhesive Gel, in Women with Secondary Amenorrhea, Abstract, Presented at the 8th International Congress on the Menopause, Sydney, Australia,* 1996.

FIG. 3 illustrates the bleeding pattern produced by a 90 mg. dose of progestin (CRINONE® 8% progesterone gel) cyclically administered every other day vaginally, also as reported in Warren, M. P., et al., *Evaluation of Crinone® . . .*, cited above.

DETAILED DESCRIPTION OF THE INVENTION

The present invention is related to a method of treating with progestins comprising use of a therapeutically effective amount of progestin for vaginal administration to menopausal and post-menopausal women in an improved regimen in order to promote regular withdrawal bleeding. Daily vaginal dosing of CRINONE® 4% progesterone gel to estrogenized women was demonstrated to produce endometrial transformation, but with monthly withdrawal bleeding consistently and predictably occurring only after the progestin administration is complete—only upon true "withdrawal" from the progestin administered.

The present invention is also related to a method of treating with progestins comprising use of a therapeutically effective amount of progestin for vaginal administration to menopausal and post-menopausal women in an improved regimen for maintaining amenorrhea. Constant rather than cyclical association of estrogens and progestins is proposed in menopausal and post-menopausal women in order to avoid monthly withdrawal bleeding altogether. Azzawi, A. J., de Ziegler, D., *Vaginal Progesterone Gel-based Continuous Combined HRT as an Amenorrheic Regimen, Presented at IV European Congress on Menopause,* Vienna, October 1997. Constant, or regular, administration of progestins throughout the month, without break, promotes amenorrhea, or a total lack of bleeding. However, just as with pregnancy-induced amenorrhea, constant administration of progestins does not produce the often-desired physiological endometrial changes associated with the menstrual cycle, during which the endometrium undergoes monthly transformation and shedding. Instead, the endometrium undergoes a maintained state of atrophy.

Even when endometrial atrophy, and thus amenorrhea, are desired to be maintained, continuous daily vaginal administration of progestins is impractical and inconvenient. We also have studied the sustained release properties of the progestin gel described in the '150 Patent, and achieved constant uterine exposure to constant administration of progesterone while limiting vaginal applications to a reasonable twice a week. CRINONE® 8% progesterone gel, available from Wyeth-Ayerst Laboratories, of Philadelphia, Pa., was shown to maintain amenorrhea upon bi-weekly dosing to women already receiving constant transdermal estrogen therapy. This administration achieved and maintained endomettial atrophy as expressed by the high incidence of amenorrhea and thin endometrium as revealed by ultrasound examination. This simple, easy regimen, devoid of the common side effects and problems encountered with synthetic progestins or oral administration, is a new-clinical option for menopausal and post-menopausal women wishing to avoid withdrawal bleeding altogether while receiving progestins. See, Fanchin, R., de Ziegler, D., et al., *Transvaginal Administration of Progesterone: Dose-response Data Support a First Uterine Pass Effect, Obstet. Gynecol.,* 90: 396–401 (1997).

Contrary to other administrations of progestin discussed in the art, the regimen of daily cyclical treatment with progestin produced reliable, regular withdrawal bleeding only after the progestin administration period. This provides substantial convenience to women on progestin therapy, without the uncertainty and inconvenience of irregular and unpredictable onset of bleeding. And the regimen of constant treatment with progestin maintained complete amenorrhea. This provides convenience to women seeking amenorrhea, without the periodic breakthrough bleeding or spotting common for three to six months with other methods of treatment.

The invention comprises use of a progestin formulation for daily vaginal administration while promoting regular withdrawal bleeding after monthly progestin administration is completed, or for constant vaginal administration while maintaining complete amenorrhea. Preferably, the progestin formulation comprises progesterone and a bioadhesive carrier, which may be in a gel formulation, containing a polymer base designed to give controlled and prolonged release of the progesterone through the vaginal mucosa. This route of administration also avoids first-pass metabolism problems as well as many significant adverse events.

The present invention comprises a dosing regimen and manner of treating with erogestin in hormone replacement therapy. Preferably, about 45 mg to 90 mg of progesterone is administered at one time. The composition for cyclical administration is preferably administered daily for part of each cycle, which preferably is based on calendar months for convenience. The composition for constant administration is preferably administered about twice per week. Most preferably, only natural progesterone itself is used.

The specific drug delivery formulations preferred, which were chosen and used in Examples 1 and 2, CRINONE® 8% and 4% progesterone gels from Wyeth-Ayerst Laboratories, Philadelphia, Pa., comprise cross-linked polycarboxylic acid polymer formulations, generally described in U.S. Pat. No. 4,615,697 to Robinson (hereinafter "the '697 patent") and in the '150 Patent, each of which is incorporated herein by reference. In general, at least about eighty percent of the monomers of the polymer in such a formulation should contain at least one carboxyl functionality. The cross-linking agent should be present at such an amount as to provide enough bioadhesion to allow the system to remain attached to the target epithelial surfaces for a sufficient time to allow the desired dosing to take place.

For vaginal administration, such as in the examples below, preferably the formulation remains attached to the epithelial surfaces for a period of at least about twenty-four to forty-eight hours. Such results may be measured clinically over various periods of time. This preferred level of bioadhesion is usually attained when the cross-linking agent is present at about 0.1 to 6.0 weight percent of the polymer, with about 1.0 to 2.0 weight percent being most preferred, as long as the appropriate level of bioadhesion results. Bioadhesion can also be measured by commercially available surface tensiometers utilized to measure adhesive strength.

The polymer formulation can be adjusted to control the release rate of the progesterone by varying the amount of cross-linking agent in the polymer. Suitable cross-linking agents include divinyl glycol, divinylbenzene, N,N-diallylacrylamide, 3,4-dihydroxy-1,5-hexadiene, 2,5-dimethyl-1,5-hexadiene and similar agents.

A preferred polymer for use in such a formulation is Polycarbophil, U.S.P., which is commercially available from B.F. Goodrich Speciality Polymers of Cleveland, Ohio under the trade name NOVEON®-AA1. The United States Pharmacopeia, 1995 edition, United States Pharmacopeial Convention, Inc., Rockville, Md., at pages 1240–41, indicates that polycarbophil is a polyacrylic acid, cross-linked with divinyl glycol.

Other useful bioadhesive polymers that may be used in such a drug delivery system formulation are mentioned in the '697 patent. For example, these include polyacrylic acid polymers cross-linked with, for example, 3,4-dihydroxy-1, 5-hexadiene, and polymethacrylic acid polymers cross-linked with, for example, divinyl benzene.

Typically, these polymers would not be used in their salt form, because this would decrease their bioadhesive capability. Such bioadhesive polymers may be prepared by conventional free radical polymerization techniques utilizing initiators such as benzoyl peroxide, azobisisobutyronitrile, and the like. Exemplary preparations of useful bioadhesives are provided in the '697 patent.

The bioadhesive formulation may be in the form of a gel, cream, tablet, pill, capsule, suppository, film, or any other pharmaceutically acceptable form that adheres to the mucosa and does not wash away easily. Different formulations are further described in the '697 Patent, which is incorporated herein by reference.

Additionally, the additives taught in the '697 patent may be mixed in with the cross-linked polymer in the formulation for maximum or desired efficacy of the delivery system or for the comfort of the patient. Such additives include, for example, lubricants, plasticizing agents, preservatives, gel formers, tablet formers, pill formers, suppository formers, film formers, cream formers, disintegrating agents, coatings, binders, vehicles, coloring agents, taste and/or odor controlling agents, humectants, viscosity controlling agents, pH-adjusting agents, and similar agents.

A preferred progestin composition is CRINONE® 4% or 8% progesterone gel, which consists of the following ingredients discussed further in the '150 Patent: 4 or 8 weight percent progesterone, 12.9 weight percent glycerin, 4.2 weight percent mineral oil, 2 weight percent polycarbophil (available from B. F. Goodrich Specialty Polymers of Cleveland, Ohio), 1 weight percent hydrogenated palm oil glyceride, 1 weight percent carbomer 934P (available from B. F. Goodrich), 0.08 weight percent sorbic acid, 0–2 weight percent sodium hydroxide, and the remaining part purified water. (This is the same basic formula discussed in the '150 Patent at column 6, lines 44–52, except that methylparaben is not presently included.)

Sorbic acid is a preservative, which may be substituted by any other approved preservative, such as methylparaben, benzoic acid or propionic acid.

Carbomer 934P is a gel former, which may be substituted by other gel formers, such as carbomer 974P, carbomer'980, methyl cellulose or propyl cellulose.

Glycerin is a humectant; alternative humectants include, for example, propylene glycol or dipropylene glycol.

Mineral oil and hydrogenated palm oil glyceride are lubricating agents; alternatives include, for example, any mineral or vegetable oil, such as canola oil, palm oil, or light mineral oil.

Sodium hydroxide is simply a strong base for purposes of controlling the pH level; other bases commonly used for that purpose may be substituted.

Preparation of the formulation involves hydration of the polymers, separate mixing of water-soluble ingredients (the "polymer phase") and oil-soluble ingredients (the "oil phase"), heating and mixing of the two phases, and homogenization of the mixture. All ingredients listed above are well-known and readily available from suppliers known in the industry.

The polymer phase may generally be prepared by mixing the water, sorbic acid, polycarbophil, and carbomer are added. The polymers are hydrated by mixing for several hours, generally about 2–3 hours until a uniform, smooth, homogenous, lump-free gel-like polymer mixture is obtained. When the polymers are completely hydrated, the progesterone is added and mixed in, until a homogeneous suspension is obtained.

The oil phase is generally prepared by melting together the glycerin and mineral oil, by heating to 75 to 78° C. The mixture is cooled to about 60° C., while the polymer phase is warmed to about the same temperature. The polymer phase is then added to the heated oil phase. The two phases are mixed thoroughly, producing a uniform, creamy white product. If needed, mix in sodium hydroxide to produce a pH of about 2.5–3.5, generally about 3. When the mixture has cooled, it is de-aerated. The resulting product is aseptic because of the nature of the preparation and pH as well as the presence of the preservative.

As will be apparent to those skilled in the art, the composition of the formulation can be varied to affect certain properties of the formulation. For example, the concentration of the bioadhesive polymer can be adjusted to provide greater or lesser bioadhesion. The viscosity can be varied by varying the pH or by changing the concentration of the polymer or gel former. The relative concentrations of the oils compared to the water can be varied to modulate the release rate of the progestin from the drug delivery system. The pH can also be varied as appropriate or to affect the release rate or bioadhesiveness of the formulation.

The progestin formulation may be delivered vaginally in any of a variety of fashions known in the art, such as by plunger, douche, suppository, or manually. A preferred method of delivery is using a device such as that described in U.S. Pat. No. Des. D345,211 or U.S. Pat. No. Des. D375,352, which disclosures are incorporated herein by reference. Such a device is an oblong hollow container, with one end capable of being opened and the other end containing most of the composition to be delivered and capable of being squeezed. Such devices allow for pre-measurement of the amounts of product to be delivered in a single dosage by a sealed container which may be used relatively easily. The containers also maintain the product in an aseptic environment until use. Upon use the container is opened and the open end is inserted into the vagina, while the other end is squeezed to expel the contents of the container into the vagina. A 'kit' of the product can therefore contain a single dose or multiple doses of the product.

EXAMPLE 1

Daily vs. Twice-Weekly Cyclical, and Constant, Administration of Progesterone

This study was designed to examine the use of CRINONE® progesterone gel in menopause as part of hormone replacement therapy ("HRT") in cyclical association with estrogen therapy, and in constant combined association with estrogen for a no-bleed regimen. The results from the first groups of subjects in the study are reported here. (The study continued with additional subjects; complete results from all subjects, including those discussed in Example 1, are reported below at Example 3.)

Two groups of women were assembled, each with 20 women. Group I ranged in age from 38 to 55 years old, and each woman exhibited menopausal symptoms or was already on HRT. Group II ranged in age from 50 to 64, and each woman was more than 3 years into menopause (amenorrhea), or on HRT with cyclical bleeding. None of the woman in either group exhibited abnormal bleeding or any other uterine pathology.

Group I received estrogen continuously (PREMARIN® (0.625 mg) conjugated estrogens (Wyeth-Ayerst Laboratories, Philadelphia, Pa.), PROGYNOVA® (2 mg) estradiol valerate (Schering A. G., Berlin, Germany), or ESTRADERM® TTS (50 mg) or ESTRADERM® MX 0.05 (0.050 mg) estrogen patches (Novartis Pharmaceutical, Basel, Switzerland)), and CRINONE® 4% progesterone gel (45 mg. progesterone) every day in the morning from cycle days 15 to 24. (For practical purposes and convenience, administration took place monthly on calendar days 1 to 10, corresponding to cycle days 15 to 24.), Group II received ESTRADERM® Mx (50 mg) estrogen patch (Novartis Pharmaceutical) twice-weekly, continuously (or if intolerant to the patch, OESTROGEL® estrogen gel (Besins-Iscovesco Laboratories, Paris, France) every day), and CRINONE® 8% progesterone gel (90 mg progesterone) twice a week in the morning, continuously.

For all subjects, the baseline clinical assessment included a clinical exam, and a vaginal ultrasound to screen for women on no pre-existing treatment less than 5 mm thick, and for women on HRT or with persistent ovarian function less than 10 mm thick. In Group 1, the women were informed to report any vaginal bleeding other than withdrawal bleeding defined as menses-like bleeding starting after the last (tenth) progesterone dose.

Treatments were administered for at least six months. At the conclusion of the treatment, all women were again clinically examined, including a vaginal ultrasound, and endometrial sampling if the ultrasound showed for a group 1 woman an endometrium greater than 10 mm thick, or for a group 2 woman an endometrium greater than 5 mm thick. The results are reported in Charts 1 and 2 and in FIG. 1.

CHART 1

ULTRASOUND - ENDOMETRIAL THICKNESS
(mm., mean ± SEM)

| | | Baseline | | On treatment (6–12 months) |
|---|---|---|---|---|
| Group I | | 4.5 ± 1.5 | | 4.5 ± 0.8 |
| Group II | No HRT | 3.2 ± 0.6 | No bleed | 3.3 ± 1.0 |
| | HRT | 6.3 ± 1.39 | Bleeding | 3.5 ± 1.1 |

CHART 2

BLEEDING PATTERN

| Mean Age | Type of bleeding | | n | % | Disposition |
|---|---|---|---|---|---|
| Group I | | | | | |
| 46.8 ± 4.1 | Expected | Withdrawal only | 19/20 | 95 | 100% Continued HRT |
| | Abnormal | Breakthrough and/or other abnormal bleeding | 1/20 | 5 | n = 1; discontinued HRT |
| Group II | | | | | |
| 57.5 ± 4.6 | Expected | Amenorrhea (no bleed) | 15/20 | 75 | n = 13 (87%) continued HRT n = 1: changed regimen n = 1: stopped HRT |
| | Acceptable | Isolated spotting/mild bleeding | 4/20 | 20 | n = 4: all continued |
| | Unacceptable | Heavy bleeding/repeated spotting | 1/20 | 5 | n = 1: D&C Benign histology |

FIG. 1 shows the proportion of patients with bleeding, and the timing of that bleeding, for the Group 1 subjects being administered daily progesterone. In contrast, FIGS. 2 and 3 show the proportion of patients with bleeding, and the timing of that bleeding, for patients receiving, respectively, 45 mg. and 90 mg. of progesterone (CRINONE® 4% or 8% progesterone gel) every other day, as reported by Warren, et al., cited herein previously.

As detailed in Chart 2 and FIG. 1, cyclical administration to Group 1 subjects of daily CRINONE® progesterone gel resulted in 95% of the subjects experiencing withdrawal bleeding only after the monthly progestin dosing periods. Thus daily dosing profoundly changed the bleeding pattern, resulting in regular bleeding within 1 to 4 days of completing monthly progesterone treatment, with no other form of bleeding in 95% of the patients. All of these regularly-bleeding patients continued their HRT program, while the single irregularly-bleeding patient discontinued HRT-altogether.

In contrast, CRINONE® progesterone gel cyclically administered every other day produced bleeding patterns similar to those achieved with synthetic progestins (MPA), regardless of the strength of the CRINONE® progesterone gel used (4% (45 mg) or 8% (90 mg)). See Warren, et al., cited previously herein regarding CRINONE® progesterone gel and reflected in FIGS. 2 and 3, in comparison with Archer, et al., cited previously herein regarding MPA. Such a daily regimen is thus very attractive when perfect control of bleeding is desired.

For Group 2, with constant CRINONE® progesterone gel dosing, 75% of the subjects did not experience withdrawal bleeding, and only 5% (one of the twenty subjects) experienced heavy bleeding or repeated spotting. Of the 15 patients without bleeding, 13 continued their HRT program (as did all 4 of the patients with isolated spotting or mild bleeding), 1 changed her regimen and 1 stopped HRT. The sole subject with heavy bleeding or repeated spotting underwent a D&C (dilatation and curettage), with benign histology; her HRT was discontinued.

Thus, CRINONE® progesterone gel administered twice a week continuously in estrogenized menopausal woman maintained complete amenorrhea in a majority of patients. Pilot data elsewhere showed similar efficacy with CRINONE® 4% progesterone gel (45 mg. progesterone). The lack of side effects makes this regimen a very attractive option for menopausal women who do not wish to have menses. Prior regimens have often led to periodic breakthrough bleeding or spotting for three to six months. women had an endometrium less than 5 mm thick. Of the 13 amenorrheic women, 10 were satisfied and continued their treatment, 2 switched to a different HRT regimen and 1 stopped HRT altogether.

Again, CRINONE® progesterone gel administered continuously, twice a week, maintained complete amenorrhea in a majority of patients.

EXAMPLE 3

Daily vs. Twice-Weekly Cyclical, and Constant, Administration of Progesterone

In a continuation of the study reported above in Example 1, this study continued to examine the use of CRINONE® progesterone gel in menopause as part of hormone replacement therapy ("HRT") in cyclical association with estrogen therapy, and in constant combined association with estrogen for a no-bleed regimen. Group I included a total of 69 women, of which were the women from Group I of Example 1 and Group II included a total of 67 women. 20 of which were the women from Group II of Example 1; Group II women were more than three years into menopause, or more than 53 years of age, and free of bleeding disorders. The 47 new women in Group II were given CRINONE 4% progesterone gel instead of the 8% given to the original 20 women from Group II of Example 1.

Women in both groups were evaluated after six months of treatment, and at six-month intervals thereafter. Endometrial thickness was evaluated on ultrasound, and the results through eighteen months of treatment are reported at Chart 3. Bleeding patterns through six months are reported at Chart 4 for the 49 new women of Group I and the 47 new women of Group II. In a subset of fourteen women from the 49 new women of Group I evaluated at eighteen months, twelve remained amenorrheic for the entire observation period.

CHART 3

| | ULTRASOUND - ENDOMETRIAL THICKNESS (mm., mean ± SEM) | | | |
|---|---|---|---|---|
| | | Baseline | | On treatment (6–18 months) |
| Group I | | 4.1 ± 1.5 | | 4.9 ± 0.9 |
| Group II | No HRT | 3.7 ± 0.7 | No bleed | 3.9 ± 1.2 |
| | HRT | 6.7 ± 1.45 | Bleeding | 3.8 ± 1.76 |

CHART 4

| | BLEEDING PATTERN | | | |
|---|---|---|---|---|
| Mean Age | | Type of bleeding | n | % |
| Group I | | | | |
| 50 ± 1.5 | Expected | Withdrawal only | 44/49 | 89.8 |
| | Abnormal | Breakthrough and/or other abnormal bleeding | 5/49 | 10.2 |
| Group II | | | | |
| 58 ± 24.5 | Expected | Amenorrhea (no bleed) | 39/47 | 83.0 |
| | | | 5/47 | 10.6 |
| | Acceptable | Isolated spotting/ mild bleeding | 3/47 | 6.4 |
| | Unacceptable | Heavy bleeding/ repeated spotting | | |

Consistent with Chart 2 and FIG. 1 discussed above in Example 1, Chart 4 demonstrates that administration to Group 1 subjects of daily CRINONE® progesterone gel resulted in 89.8% (44 out of 49) of the subjects experiencing withdrawal bleeding only after each of the six monthly progestin dosing periods. Thus daily dosing profoundly changed the bleeding pattern, resulting in regular bleeding within 1 to 4 days of completing monthly progesterone treatment, with no other form of bleeding in 89.8% of the patients. Of the 63 women of Group I in toto, fifty eight, or 92%, elected to remain on the vaginal progesterone for HRT, two opted for another treatment option and three discontinued all hormone treatment.

For Group 2 subjects, with constant CRINONE® progesterone gel dosing, 83.0% of the subjects did not experience withdrawal bleeding, only 6.4% experienced heavy bleeding or repeated spotting, and 0.6% experienced isolated spotting or mild bleeding at anytime during the six-month evaluation period.

Thus, results from the larger pool of test subjects (relative to the first groups reported above at Example 1) further demonstrates that progestin administered twice a week continuously in estrogenized menopausal woman maintained complete amenorrhea in the vast majority of test subjects. And the cyclical daily administration of progestin in woman undergoing HRT provided much more reliable and regular withdrawal bleeding. Especially in combination with the lower incidence of side effects, either regimen should lead to improved HRT compliance.

Any and all publications, patents, and patent applications mentioned in this specification are indicative of the level of skill of those skilled in the art to which this patent pertains. All publications, patents, and patent applications are herein incorporated by reference to the same extent as if each individual publication, patent, or patent application was specifically and individually indicated to be incorporated by reference.

Reasonable variations, such as those which would occur to a skilled artisan, can be made without departing from the spirit and scope of the invention.

We claim:

1. A method of promoting regular withdrawal bleeding in a woman undergoing cyclical progestin administration comprising daily, cyclical vaginal delivery of progestin via a drug delivery system in an amount sufficient to cause secretory transformation of the endometrium without causing the typical side effects associated with progestin administration, wherein the drug delivery system comprises a water-soluble, water-swellable cross-linked polycarboxic acid polymer.

2. The method of claim 1 wherein the drug delivery system comprises a water-insoluble, water-swellable cross-linked polycarboxylic acid polymer.

3. The method of claim 2 wherein the polymer is polycarbophil.

4. The method of claim 3 wherein the progestin is progesterone.

5. The method of claim 4 wherein the amount of progesterone delivered is about 45 mg to about 90 mg per dose.

6. The method of claim 4 wherein the drug delivery system additionally comprises at least one adjuvant.

7. The method of claim 2 wherein the drug delivery system is administered daily during a set portion of every calendar month.

8. The method of claim 3 wherein the woman is also being treated with estrogen.

9. The method of claim 7 wherein the woman is also being treated with estrogen.

10. The method of claim 5 wherein the drug delivery system is administered daily during a set portion of every calendar month.

11. The method of claim 10 wherein the woman is also being treated with estrogen.

* * * * *

UNITED STATES PATENT AND TRADEMARK OFFICE
CERTIFICATE OF CORRECTION

PATENT NO. : 6,593,317 B1
DATED : July 15, 2003
INVENTOR(S) : de Ziegler et al.

It is certified that error appears in the above-identified patent and that said Letters Patent is hereby corrected as shown below:

Title page, Item [54] and Column 1, line 1,
Change the title to -- PROGESTIN THERAPY TO PROMOTE REGULAR WITHDRAWAL BLEEDING --.

Title page,
Item [56], References Cited, OTHER PUBLICATIONS, make the following changes:
"Bulleti, C. et al.," reference, change "Bulleti" to -- Bulletti --; change "effects" to
-- effect --; and after "Human Reproduction", delete the second ",".
"Clisham, P.R. et al.," reference, before "Obstetrics & Gynecology" delete "Acta".
Delete the "Babiba, M.A. et al.," reference and substitute therefore the following references:
-- Habiba, M.A. et al., "Endometrial responses to hormone replacement therapy: the bleeding pattern," Human Reproduction, Vol. 11, No. 3 (1996) 503-508.
Hahn, R.G., "Compliance considerations with estrogen replacement: Withdrawal bleeding and other factors," Am. J. Obstet. Gynecol, vol. 161, No. 6, Part 2 (Dec. 1989) 1854-1858. --.
"Magos, A.L. et al.," reference, change "Woment" to -- Women --.
"Marslew, U. et al.," reference, change "estrogen-progesterone" to
-- estrogen-progestogen --.
"Navot, D. et al.," reference, (first occurrence) change "Prognancies" to
-- Pregnancies --.
"Navot, D. et al.," reference, (second occurrence) after "through" insert -- the --.
"Rosano, G.M.C. et al.," reference, (first occurrence) after "17beta" insert -- upon --.
"Rosano, G.M.C. et al.," reference, (second occurrence) change "Australis" to
-- Australia --.
"Simon, J.A. et al.," reference, change "proportinality" to -- proportionality --.
After the "Sitruk-Ware, L.R. et al.," reference, insert the following references:
-- Sitruk-Ware, R. et al., "Oral Micronized Progesterone-Bioavailability pharmacokinetics, pharmacological and therapeutic implications – a review," Contraception, Vol. 36, No. 4 (Oct. 1987) 373-402. --.
Delete the "Villanueva, B. et al.," reference and substitute therefore the following references:
-- Villanueva, B. et al., "Intravaginal Administration of Progesterone: Enhanced Absorption after Estrogen Treatment," Fertility and Sterility, Vol. 35, No. 4 (April 1981) 433-437.
P. Wardle et al., "Pilot Study of Continuous Combined Postmenopausal HRT Using Alternate Day or Twice Weekly Vaginal Progesterone" MATURITAS, Vol. 27, No. Suppl, F015, 1997, Page 47 XP002094218. --.

UNITED STATES PATENT AND TRADEMARK OFFICE
CERTIFICATE OF CORRECTION

PATENT NO.    : 6,593,317 B1
DATED         : July 15, 2003
INVENTOR(S)   : de Ziegler et al.

It is certified that error appears in the above-identified patent and that said Letters Patent is hereby corrected as shown below:

OTHER PUBLICATIONS, cont'd
"Warren, M.P. et al.," reference, change "eta l." to -- et al. --.
Delete the "Weinstein, M. et al.," reference and substitute therefore the following references:
-- Weinstein L. et al., "Evaluation of a continuous combined low-dose regime of estrogen-progestin for treatment of the menopausal patient," Am J Obstet Gynecol, Vol. 162, No. 6 (June 1990) 1534-1539.
Whitehead, M. et al., "Hormone Replacement Therapy Your Questions Answered," (Churchill Livingstone Publishers, Edinburgh 1992), Chapters 5 & 9. --.
"Casper, R.F.," reference, change "vol. 4(1)" to -- vol. 41(1) --.

Column 1,
Line 37, change "in vitro" to -- *in vitro* --.

Column 4,
Line 41, change "endomettial" to -- endometrial --.

Column 5,
Line 9, change "erogestin" to -- progestin --.

Column 6,
Line 38, change "carbomer'980" to -- carbomer 980 --.

Column 9,
Line 44, after "six months.", delete "women".
Delete lines 45-51.
Line 53, change "EXAMPLE 3" to -- EXAMPLE 2 --.
Line 64, change "women, of which" to -- women, 20 of which --.
Line 65, change "women. 20 of which" to -- women, 20 of which --.
Line 66, change "Example 1; Group II" to -- Example 1. Group II --.

Column 10,
Line 38, CHART 4, under the heading "Group II"), change "58 ± 24.5" to -- 58.2 ± 4.5 --.
Line 62, change "0.6%" to -- 10.6% --.

UNITED STATES PATENT AND TRADEMARK OFFICE
CERTIFICATE OF CORRECTION

PATENT NO.    : 6,593,317 B1
DATED         : July 15, 2003
INVENTOR(S)   : de Ziegler et al.

It is certified that error appears in the above-identified patent and that said Letters Patent is hereby corrected as shown below:

Column 11,
Line 25, change "polycarboxic" to -- polycarboxylic --.

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,593,317 B1
DATED         : July 15, 2003
INVENTOR(S)   : de Ziegler et al.

It is certified that error appears in the above-identified patent and that said Letters Patent is hereby corrected as shown below:

Column 11,
Line 25, delete "water-soluble" and insert -- water-insoluble --.

Column 12,
Delete lines 1-3 comprising claim 2.
Lines 4 and 12, after "The method of claim", delete "2" and insert -- 1 --.

Signed and Sealed this

Seventeenth Day of May, 2005

JON W. DUDAS
*Director of the United States Patent and Trademark Office*